United States Patent [19]

Lyons et al.

[11] 4,156,783

[45] May 29, 1979

[54] CONVERSION OF BENZYLIDENE DIACETATE TO PHENYL ACETATE AND METHYLENE DIACETATE

[75] Inventors: James E. Lyons, Wallingford; Robert W. Shinn, Aston; George Suld, Springfield, all of Pa.

[73] Assignee: Suntech, Inc., Philadelphia, Pa.

[21] Appl. No.: 890,180

[22] Filed: Mar. 27, 1978

[51] Int. Cl.$^2$ ............................................. C07C 69/14
[52] U.S. Cl. ................................... 560/131; 560/130; 560/263
[58] Field of Search ...................... 560/131, 130, 263

[56] References Cited

U.S. PATENT DOCUMENTS 2,799,698   7/1957   Taves .................................. 560/131

Primary Examiner—Jane S. Myers
Attorney, Agent, or Firm—J. Edward Hess; Donald R. Johnson; Stanford M. Back

[57] ABSTRACT

Benzylidene diacetate may be converted to phenyl acetate and methylene diacetate by an acid-catalyzed reaction in the presence of oxygen or air, and acetic anhydride, at elevated temperatures and pressures.

6 Claims, No Drawings

CONVERSION OF BENZYLIDENE DIACETATE TO PHENYL ACETATE AND METHYLENE DIACETATE

BACKGROUND OF THE INVENTION

This invention relates to a process for the preparation of phenyl acetate and methylene diacetate. More particularly, this invention relates to the conversion of benzylidene diacetate to phenyl acetate and methylene diacetate by an acid catalyzed reaction in the presence of acetic anhydride and air or oxygen at elevated temperatures. Both phenyl acetate and methylene diacetate are known articles of commerce: the former is a staple article of commerce used as a solvent and as an organic intermediate; the latter material can be used as a high octane fuel component, or as an intermediate in the preparation of formaldehyde.

No art has been found which bears on this novel process.

SUMMARY OF THE INVENTION

As aforestated, the process of this invention comprises reacting benzylidene diacetate in acetic anhydride in the presence of air or oxygen and an acid catalyst at elevated temperatures to yield phenyl acetate and methylene diacetate in accordance with the following reaction:

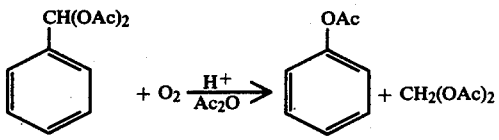

DESCRIPTION OF THE INVENTION

One method for preparing the benzylidene diacetate starting material is by the acid catalyzed reaction of benzaldehyde with acetic anhydride disclosed in J.A.C.S., 72, 847 (1950).

The process of this invention is conveniently carried out under elevated temperatures of from about 150° to 250° C., preferably 200° to 220° C., and initial pressures at room temperature, of from about 100 to 300 psig, of an $O_2$-containing gas, preferably 190 to 220 psig, in an autoclave for periods ranging from about 15 minutes to 4 hours, depending upon the pressures and temperatures employed.

The benzylidene diacetate, (5–25 wt.%) should desirably be reacted in a solvent such as benzene. The acetic anhydride should desirably be present in amounts of 2–3 times by weight of the amount of benzylidene diacetate used. The amount of acid catalyst employed should be in concentrations ranging from about $10^{-1}$ to $10^{-2}$, preferably $2 \times 10^{-2}$ to $4 \times 10^{-2}$, moles/liter.

Air may be used in place of $O_2$, in which case the amounts are increased proportionately to provide an equivalent amount of $O_2$.

The acid catalyst is desirably sulfuric acid, but other like acids such as peroxymonosulfuric acid, Caro's dry reagent, or mixtures thereof, may be used instead.

If desired, small amounts of initiators such as azobisisobutyronitrile, dibenzoylperoxide and the like may be added to help initiate the reaction. Generally, 0.2 wt.%, is sufficient for this purpose.

The following examples are provided to illustrate, but not to limit, the scope of the invention described herein.

EXAMPLES

The following reactions were run in a rocking autoclave under pressure (145 psi of 20% $O_2$ in $N_2$) using sulfuric acid (0.11 gms) as the catalyst, acetic anhydride (11.4 ml) and benzylidene diacetate (4 gms) in benzene (50 ml) for the time indicated at the temperature shown in the table. The analyses were carried out by gas chromatography.

Table 1

| Example | Reaction Time, Hrs. | Reaction Temp., °C. | Conversion of PHCH(OAc)$_2$ | % PhOAc In Reaction Mixture | % CH$_2$(OAc)$_2$ In Reaction Mixture |
|---|---|---|---|---|---|
| 1 | 0.5 | 200 | 99 | 21% | 25% |
| 2 | 1.0 | 200 | 99 | 22% | 23% |
| 3 | 1.0 | 170 | 78 | 8% | 8% |

The phenyl acetate and methylene diacetate may be recovered and separated by routine methods, as for example by distillation.

The invention claimed is:

1. A process for the production of phenyl acetate and methylene diacetate which comprises reacting benzylidene diacetate with air or oxygen at elevated temperatures and pressures in the presence of acetic anhydride and an acid catalyst.

2. The process of claim 1 wherein the acid catalyst is sulfuric acid.

3. The process of claim 1 wherein the temperature is in the range of 150° to 250° C.

4. The process of claim 1 wherein the initial pressure, at room temperature, is from about 100 to 300 psig.

5. The process of claim 1 wherein the acid catalyst is present in amounts of $10^{-1}$ to $10^{-2}$ moles/liter.

6. The process of claim 1 wherein the acetic anhydride is present in amounts of 2–3 times by weight of the benzylidene diacetate.